United States Patent
Van Pelt

(10) Patent No.: US 8,163,177 B2
(45) Date of Patent: Apr. 24, 2012

(54) DELIVERY AND ASSESSMENT SYSTEM FOR THE AUTOMATED MANUFACTURING OF HIGH PERFORMANCE NANOFLUIDIC SEPARATION DEVICES

(76) Inventor: Colleen K. Van Pelt, Groton, NY (US)

( * ) Notice: Subject to any disclaimer, the term of this patent is extended or adjusted under 35 U.S.C. 154(b) by 817 days.

(21) Appl. No.: 12/275,335

(22) Filed: Nov. 21, 2008

(65) Prior Publication Data
US 2009/0151808 A1 Jun. 18, 2009

Related U.S. Application Data

(60) Provisional application No. 60/989,581, filed on Nov. 21, 2007.

(51) Int. Cl.
*B01D 15/08* (2006.01)
(52) U.S. Cl. ............... 210/198.2; 210/656; 210/143
(58) Field of Classification Search .......... 210/635, 210/656, 198.2, 502.1; 141/12, 80
See application file for complete search history.

(56) References Cited

U.S. PATENT DOCUMENTS

| | | | |
|---|---|---|---|
| 6,401,555 B1 * | 6/2002 | Bowers | 73/866.5 |
| 7,261,812 B1 * | 8/2007 | Karp et al. | 210/198.2 |
| 2003/0026740 A1 | 2/2003 | Staats | |
| 2003/0150806 A1 * | 8/2003 | Hobbs et al. | 210/635 |
| 2005/0032238 A1 * | 2/2005 | Karp et al. | 436/177 |
| 2005/0242017 A1 | 11/2005 | Staats | |

FOREIGN PATENT DOCUMENTS

KR 1020040009553 A 1/2004

OTHER PUBLICATIONS

PTO Translation No. 12-0725 of Korean Patent No. 1020040009553.*

* cited by examiner

*Primary Examiner* — Ernest G Therkorn
(74) *Attorney, Agent, or Firm* — Nixon Peabody LLP

(57) ABSTRACT

A multi-column packing system and packed bed assessment system for producing small bore LC columns of superior quality, improved column-to-column reproducibility, and lower cost than current commercially available columns. The process utilizes an automated multi-column packing system with an integrated sensor that detects when the slurry-packed bed has reached the desired length. The optical packed bed assessment system examines the packed bed within the column and detects any packing inconsistencies or voids within the column. The multi-column packing system makes automated connections to tubes via an automated compression mechanism.

11 Claims, 9 Drawing Sheets

DELIVERY AND ASSESSMENT SYSTEM FOR THE AUTOMATED MANUFACTURING OF HIGH PERFORMANCE NANOFLUIDIC SEPARATION DEVICES

CROSS-REFERENCE TO RELATED APPLICATIONS

This application claims priority from U.S. Provisional Patent Application Ser. No. 60/989,581, filed Nov. 21, 2007 the contents of which are incorporated by reference.

FIELD OF THE INVENTION

The present invention relates generally to chromatography and fluidic systems, and more specifically to automated column packing and the optical assessment of packed-bed columns. In one embodiment the packed-bed columns are suitable for nanofluidic applications.

BACKGROUND

Nano-liquid chromatography mass spectrometry (nanoLC/MS) has emerged as the gold standard for proteomic and glycomic laboratories. The combined nanoLC/MS technique is capable of resolving highly complex mixtures. The mixtures having components covering a wide dynamic range. The small bore LC/MS device obtains valuable mass spectral data, and is ultimately capable of identifying the components in the mixture. Furthermore, nanoLC/MS identifies, localizes, and structurally characterizes the subtle chemical variations between sample components, such as post-translational modifications.

Quantitative proteomic profiling using nanoLC/MS is an emerging technology having a great potential for the functional analysis of biological systems and for the detection of clinical diagnostic marker proteins. Quantitative proteomic profiling has been demonstrated for quantitation of proteins, as well as specifically for phosphoproteins and glycoproteins. In addition to protein identification, characterization of post-translational modifications, and quantitation of protein differential expression, nanoLC/MS is also useful for the investigation of protein-protein complexes. NanoLC/MS is a far-reaching technology, positively impacting many areas of proteomics, and consequently is invaluable to biological laboratories.

NanoLC was developed in the 1980's and has become an accepted, indispensable tool for resolving highly complex, otherwise intractable biological mixtures. NanoLC only requires attomole to femtomole sample amounts and offers high sensitivity because of the resolving power. High LC separation efficiency has resulted in 3-fold increases in the number of peptides detected by electrospray Fourier transform ion cyclotron resonance MS for proteomic analyses. Furthermore, high-efficiency separations result in narrower, sharper peaks which enables more sensitive MS detection for low abundance peptides. As a result, more complex problems are now addressable such as molecular interactions, ion structures, quantitation, and kinetics in the both the field of proteomics and glycomics.

Conventional nanoLC uses chromatography columns having inner diameters ranging from 25-150 µm. The columns are packed with 1-10 µm stationary phase particles. The most typical column has a 75 µm inner diameter and is packed with 1-5 µm particles. Typical nanoLC flow rates range from 50-700 nL/min. Smaller particle sizes and longer columns generate higher resolving power, but also increased backpressure on the system. Other low flow separation techniques including capillary electrophoresis, capillary zone electrophoresis, and capillary electrochromatography offer high sensitivity, but are difficult to couple to mass spectrometry. Furthermore, these alternative techniques have limited sample loading volumes.

Small bore LC columns are typically made by first placing a frit in a capillary and then packing the capillary with a sorbent material. The porous frits have been made from porous filters, scintering methods, restrictors and tapers including nanoelectrospray emitters, porous ceramic plugs, sol-gel technology, unions containing stainless steel screens, and self-assembled particles. Columns can be packed by a variety of different methods including dry packing, supercritical packing, electrokinetic packing, sol-gel packing, centripetal force packing, or the most widely accepted, slurry packing. A great number of variables encountered in the manufacturing of the columns affect the separation efficiency of the final product. These variables include the sorbent material itself, the type of solvent used in the packing slurry, the slurry concentration, packing pressure, and the frit type. Consequently, it is widely accepted that small bore LC column manufacturing is very difficult and can even be considered an art form. One particular problem is that voids in the packed bed that are formed within the column during manufacturing have a detrimental effect on column performance and efficiency. Therefore, the manufacturing of these small bore LC columns is challenging. Although high level research groups are able to fabricate their own small bore LC columns, the average nanoLC user must purchase columns from a commercial source.

It is evident that much of the actual manufacturing process for small bore LC columns is performed "by hand" in a non-automated fashion. Because of this, every column made by a reputable vendor undergoes rigorous and time consuming quality control testing which includes performing an analysis on each column prior to shipment. This additional testing drives up the cost of commercially available small bore LC columns. The materials used to make a small bore LC column are inexpensive. However, the manufacturing costs are 10-1000 times that of the material costs. This cost discrepancy is attributed to the labor costs of manufacturing the column, as well as its quality control testing. Even with all the time consuming quality control testing, commercially available columns still suffer from packing inconsistencies in the column bed. Evidence of column-to-column variation is observed by the fact that brand new commercial columns of the same type, produce different backpressures when installed. Furthermore, the documentation shipped with columns often make the user aware that split ratios will need to be adjusted for each individual column. Split ratio adjustment between columns is necessary due to varying backpressures caused by inconsistent packing of the column beds. An example of a packed bed defect in a commercial small bore LC column (75 µm, 3 µm particles) is shown in FIG. 1. The polyimide-coated capillary 13 contains a packed bed 12. The large void 11 in the packed bed 12 is clearly visible. The void 11 creates a detrimental effect on the column's performance. Since the columns are manufactured in a non-automated manner, there is a great variation between columns of the same type, as the numbers and sizes of the voids greatly vary throughout the columns' packed beds. This variation results in performance variation even between columns of the same type.

An automated method for both manufacturing and quality control testing small bore LC columns is desired. An automated method allows for improved column-to-column reproducibility, and lower column costs. This improved reproducibility is imperative for nanoLC to enter into the field of clinical diagnostics.

SUMMARY

Nano-liquid chromatography mass spectrometry (nanoLC/MS) is a powerful technique for proteomic and glycomic studies which is capable of not only identifying proteins and glycans from very complex mixtures, but is also able to structurally characterize differences between the components. This is particularly important for post-translational modifications. However, conventional nanoLC/MS is underutilized due to irreproducible small bore LC column performance. Therefore technology development allowing for the manufacture of columns with enhanced, reproducible performance as well as reduced column cost, permits the powerful nanoLC technique to infiltrate all biological laboratories. This enables further scientific discoveries and greater understanding of complex biological systems.

Since the high sensitivity and small sample size offered by nanoLC is needed by the majority of biological mass spectrometry users, the irreproducibility of small bore LC columns prevents the powerful nanoLC/MS technique from infiltrating the majority of biological laboratories. Identical small bore LC columns having exactly the same dimensions and stationary phase, often perform differently. This performance inconsistency between identical small bore LC columns arises from variations in particle packing within the column itself. For example, any void volumes within a packed column drastically affect its performance. The lack of consistent column-to-column performance is a barrier to widespread acceptance of the technology, particularly for nanoLC to be accepted by clinical diagnostic applications. As these variations in particle packing are introduced during the manufacturing of the columns, a technology for improving the manufacturing process is desired.

Development of both an automated method of column manufacturing, and an automated, optical packed-bed assessment device for evaluating packed beds used in nanofluidic applications is desired. The automated method allows for reproducible column packing. Furthermore, the optical assessment of the column examines the packed bed for any defects by monitoring light transmission or reflection through the column bed. Any inconsistencies in particle packing such as voids are detectable. This allows for consistently packed columns that provide uniform backpressures and performance between columns. The automated process further reduces the cost of small bore LC columns as extensive quality control testing are no longer required. Furthermore, inexpensive columns enable the potential for one-time use, disposable small bore LC columns for clinical diagnostic applications.

The automated column packing device manufactures columns with reproducibly packed beds. An integrated photoelectric sensor is utilized to terminate the packing process when the column bed reaches a desired length. The automated optical packed bed assessment system employs integrated pattern recognition software to identify bed defects such as voids. Together these two systems provide reproducibly packed, lower cost nanofluidic columns. It is understood that manufacturing and assessment processes could be either incorporated into a single instrument or divided into separate systems. The consistently packed columns provide robust, reproducible performance at a lower cost. This enables nanoLC to become an integral part of biological laboratories. This further enables scientific breakthroughs and greater understanding of complex biological systems.

BRIEF DESCRIPTION OF THE SEVERAL VIEWS OF THE DRAWINGS

The above and other objects, features, and advantages of the present invention will become more apparent when taken in conjunction with the following description and drawings wherein identical reference numerals have been used, where possible, to designate identical features that are common to the figures, and wherein.

DETAILED DESCRIPTION

Figure 1:
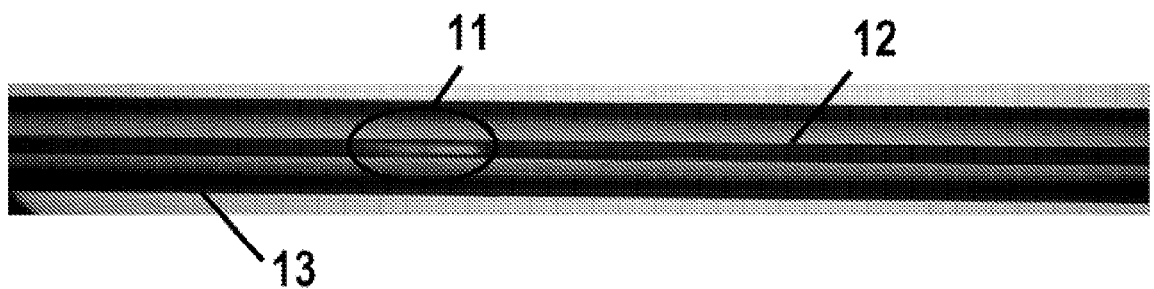
FIG. 1 is a magnified (500×) portion of a commercial 75 μm id small bore LC column from a well established vendor. The packed bed contains a void which will detrimentally affect the column's resolving efficiency and performance.

A multi-column packing system and packed bed assessment system for producing small bore LC columns of superior quality, improved column-to-column reproducibility, and lower cost than current commercially available columns are described. The process utilizes an automated multi-column packing system with an integrated sensor that detects when the slurry-packed bed has reached the desired length. The optical packed bed assessment system examines the packed bed within the column and detects any packing inconsistencies or voids within the column. The multi-column packing system makes automated connections to tubes via an automated compression mechanism. The packed bed assessment system replaces laborious and time-consuming quality control testing.

Prior to column fabrication the capillaries, such as ones having 360 μm outer diameters and 75 μm inner diameters, require preparation. It is understood that capillaries having larger or smaller, outer or inner diameters may also be used. It is also understood that the term capillary further extends to other structures for packing including fabricated channels or extruded tubes, that are either cylindrical or non-cylindrical in shape. The capillaries are prepared by first cutting a desired length. Then a porous, scintered silica frit is made at one end of the capillary. The frit is made from spherical, non-porous, non-carbon containing particles that are tapped into the outlet end of each capillary. In one embodiment the particles have a diameter of 5 μm. It is understood that particles of other sizes are suitable for use. The capillaries are then inserted into a ring-shaped filament. The filament is operated at the glass transition temperature for a period of time sufficient to scinter the silica. In one embodiment the period of time is 10 to 15 seconds. The amount of heat applied is sufficient to cause the particles to fuse together. It is important that the applied heat be neither too hot nor applied long enough to melt the particles. Melting the particles would eliminate the inter-particle spacing. The scintering step is generally fast and not rate limiting.

After the scintered frits are formed, the capillaries are ready to be placed into the automated multi-column packing system. Note that various sized capillaries and channels may be utilized as well as various methods to generate a frit. The frit may be integrated into or separate from the capillary. In one embodiment the internal diameter of the capillary ranges from 1-1000 microns and has a length from 0.01-10,000 millimeters. It is understood that the capillary may be coated or uncoated.

The packed bed assessment system technology monitors either light transmission or reflection through a column bed, detecting any inconsistencies in particle packing such as voids. The packed bed assessment provides consistently packed columns with reproducible column performance. This achieves a significant advantage over other conventional manufacturing processes as the assessment provides a quantitative inspection of packed-beds for nanofluidic devices. Furthermore the manufacturing approach reduces the cost of small bore LC columns such as nano-liquid chromatography (nanoLC) columns, as extensive quality control testing is no longer required. Reproducible column performance and lower column cost allow for the pervasive use of the technology. The automated delivery approach is further useful for delivering fluids for other process functions such as pre-treatment, post-treatment, priming, washing, derivatizations, polymerizations, modifications, grafting, pre-conditioning, and post conditioning.

In another embodiment the automated manufacturing technology developed for packing small bore LC columns is useful for packing separation channels in micro-fluidic chip-based devices. In the past the separation media most widely used in chip-based devices was monolithic in nature. Particle stationary phases are employed in chip devices, however their manufacturing proves to be difficult. Therefore it is desirable to pack micro-fluidic channels with particles in a reproducible automated fashion.

The automated packing system further allows for fluid delivery to discreet channels, capillaries, vessels, reactors, and cartridges in microchips, chromatography columns, or other devices via an automated connection system. Optionally switching valves are part of the system, but are not necessary for directing various fluids to the devices. The devices are also scalable allowing for parallel manufacturing schemes.

The automated delivery approach is further suitable for delivering fluid for other process functions such as chemical pre-treatment, post-treatment, priming, washing, derivatizations, polymerizations, modifications, grafting, pre-conditioning, and post conditioning.

Construction of the Automated Multi-Column Packing System

Figure 4:
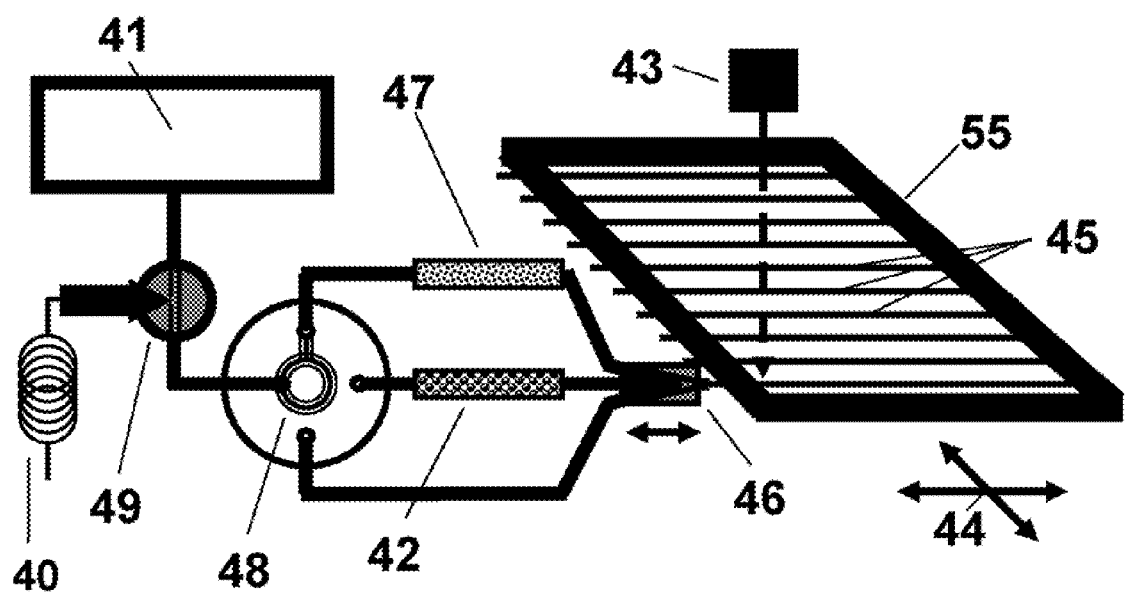
FIG. 4 is a schematic of the automated multi-column packing system. An optional backpressure release valve has been included. Arrows indicating the movement of the compression fitting mechanism and the frame jig on the translation stage are shown.

As shown in FIG. 4, the automated multi-column packing system is composed of a fluid delivery system 41, reservoirs 42 and 47 containing slurries of stationary phase particles, a frame jig 55 that holds the fritted capillaries 45, a translational stage 44, a valve 48, a bed packing sensor 43 that monitors packed bed length, a compression fitting mechanism 46, an optional pressure release valve 49 and a controller (not shown). In one embodiment the fluid delivery system contains a high-pressure pump or pressure vessel.

Figure 5A:
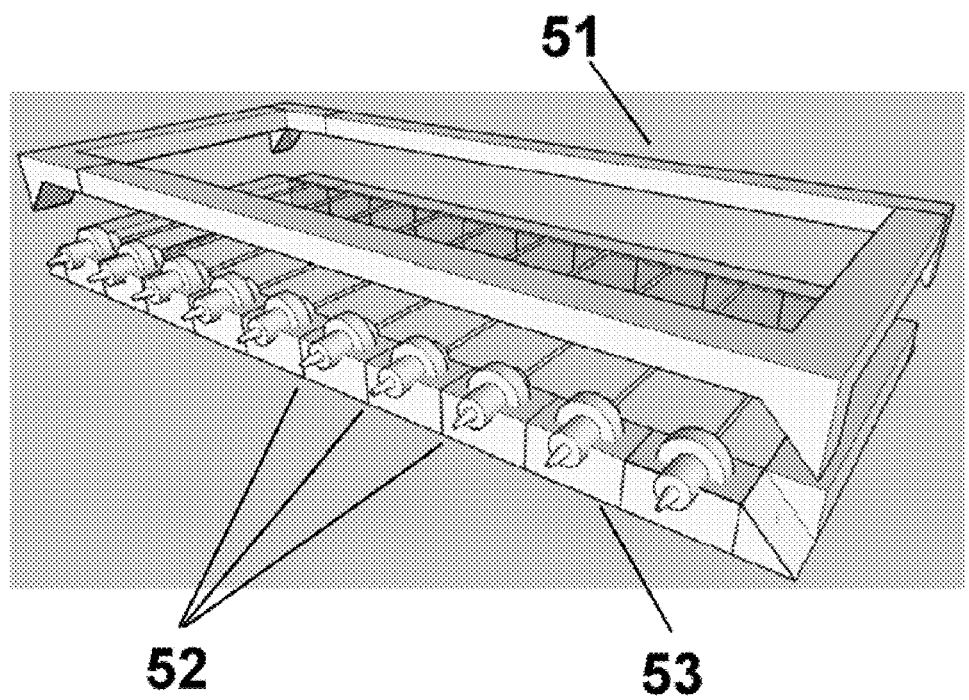
FIG. 5A shows the bottom frame has specially machined features to hold the ferrules and fritted capillaries in place. The top frame is machined in the mirror image of the bottom one. The figure is not drawn to scale as the columns and ferrules have been enlarged to be viewed more easily.
Figure 5B:
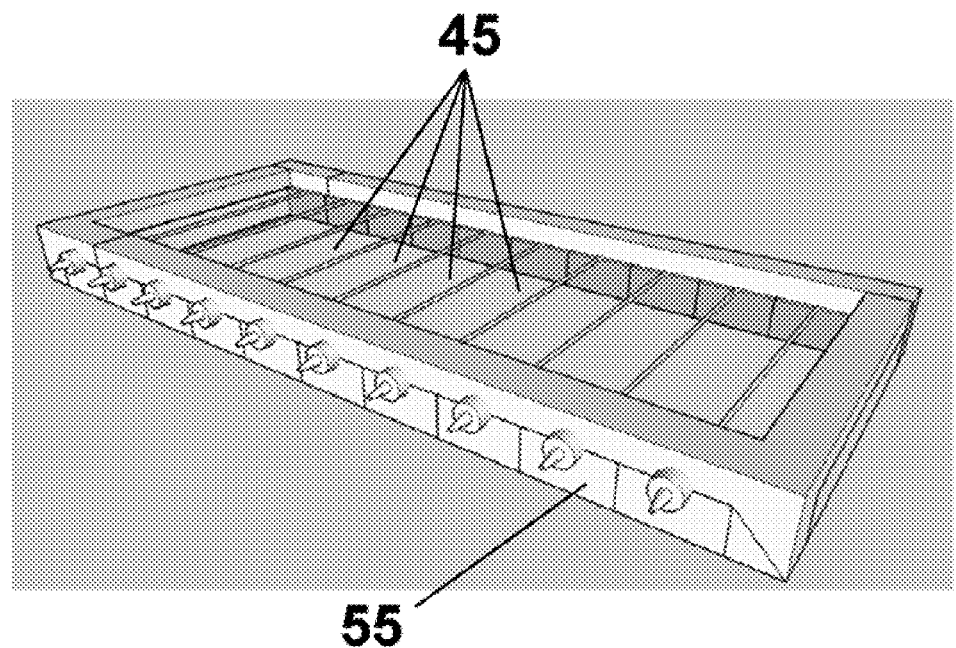
FIG. 5B shows that the top and bottom frames can be sandwiched together to form the frame jig. The ferrules and fritted capillaries are secured in place between the frames. The figure is not drawn to scale as the columns and ferrules have been enlarged to be viewed more easily.

The automated column packing system contains a removable, reusable frame jig 55 that accepts the fritted capillaries 45. As shown in FIGS. 5A-5B, the bottom frame 53 has machined grooves to hold the fritted capillaries 45 or other structure to be packed. The bottom frame 53 further contains machined features to specifically hold ferrules 52. Ferrules 52 are placed on each fritted capillary 45 and then both are positioned in the bottom frame 53 such that the capillaries 45 and ferrules 52 are located in their corresponding machined feature. The ferrule 52 is located on the capillary 45 at the opposite end from the frit. The top frame 51 is placed on top of the bottom frame, so as to sandwich the fritted capillaries 45 and ferrules 52, as shown in FIG. 5B. The top frame 51 is machined in the mirror image of the bottom frame 53 such that when in place the ferrules 52 are secured within the frame jig 55. Both frames have a large "window" where the capillaries 45 are exposed. The frame jig 55 serves to restrain the fritted capillaries 45 and ferrules 52. The frame jig 55 is specific for making columns of a particular length and it is understood that different frame jig are used for distinct column lengths. The entire frame jig (both frames, the fritted capillaries and the ferrules) is secured and locked in place on a translational stage in the automated multi-column packing system. Suitable frame materials include, but are not limited to metal, glass, or polymer and are designed such that only a very small portion (10's of microns) of the column are not be exposed in the "window" of the frame. In one embodiment the frames are reusable. In another embodiment the frames are disposable. Frames may be machined or etched from an optically transparent material so that the entire column is visible. Alternative frame, chuck, holder, jig designs may be used to correspond to the requirements of the particular parts that need to be held.

In one embodiment the channel holding component is tailored for holding substrates other than capillary, glass or polymer tubes. Substrates include reactors, vessels, cartridges, molded assemblies, microchip-based devices, micro- or nanofabricated devices composed of silicon, glass, polymers, metals, dielectrics or the like. Therefore, alternatively to tubes, the jig is capable of holding other molded, casted, machined, or microfabricated devices.

Figure 6A:
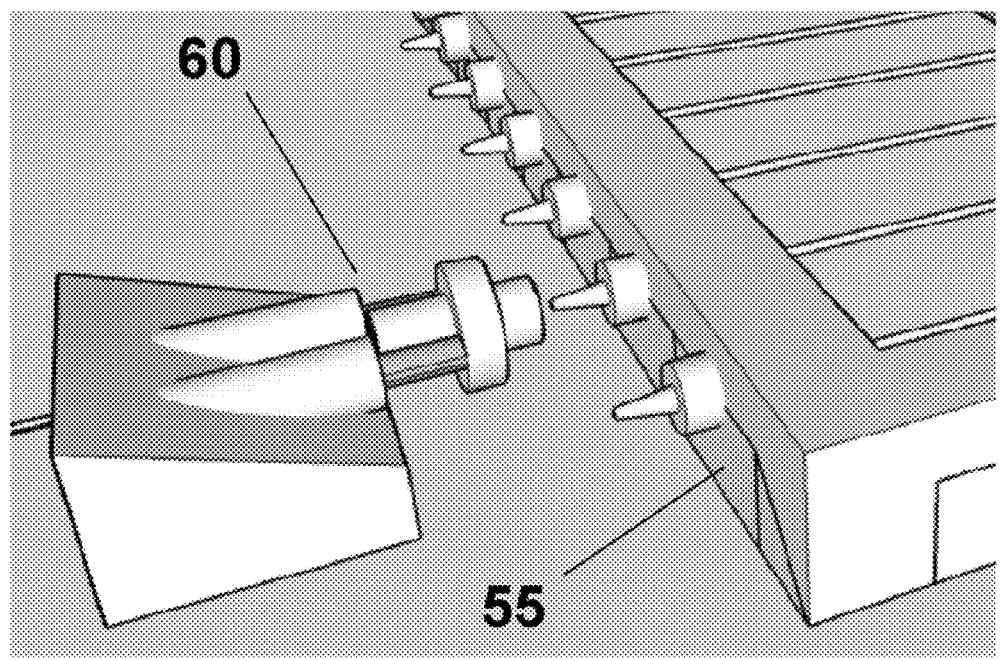
FIG. 6A shows the device before the compression connection is made to a ferrule and fritted capillary in the frame jig. The ferrules and columns have been enlarged so as to be viewed more easily.
Figure 6B:
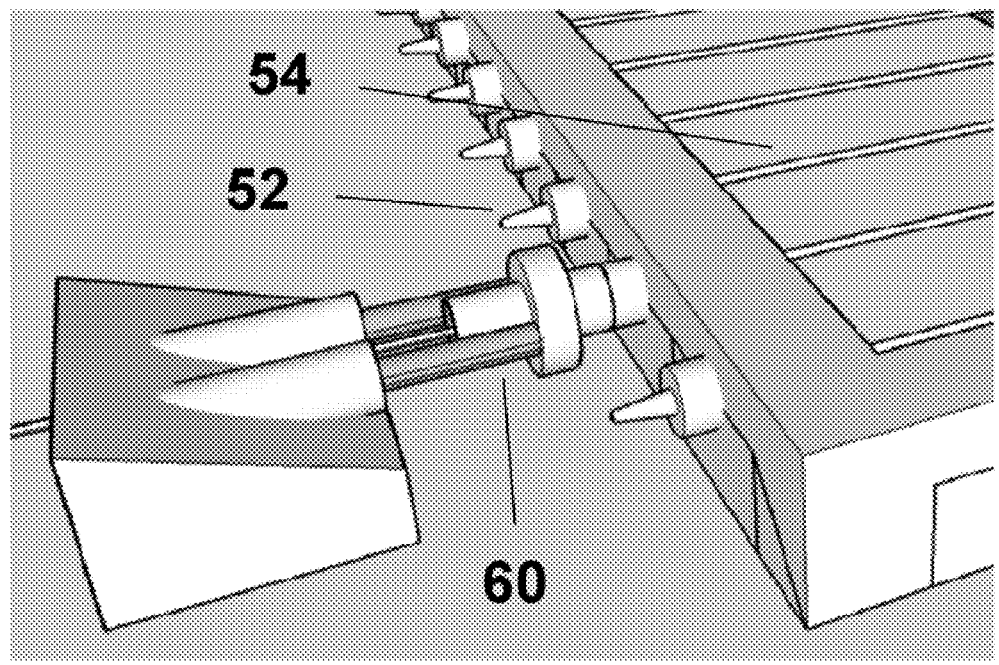
FIG. 6B shows the device after the compression connection is made to a ferrule and fritted capillary in the frame jig. The ferrules and columns have been enlarged so as to be viewed more easily.

An automated compression fitting mechanism is used to make the nanofluidic connection to the non-fritted end of the capillary. As shown in FIGS. 6A and 6B, the compression device 60 provides a continuous, axial-directed driving force to the ferrule 52 located on the fritted capillary 54. In one embodiment, the compression device 60 is a pneumatic compression device. The ferrule 52 is stationary as it is secured in place between the two frames of the frame jig 55, and the frame jig 55 is secured on a translational stage (not shown). The applied axial force compresses the ferrule against the machined, tapered receiver feature in the compression device, causing the ferrule to form a seal around the fritted capillary. The compressive force applied to make the high pressure connection is tightly controlled, eliminating the possibility of a user "over tightening" fittings which leads to leaks and fracture of capillary ends.

A further advantage of the axial-directed, torque-less compression mechanism is that connections are made by an automated process. The force needed to achieve the compression connection can be generated by pneumatic, hydraulic, mechanical clamp, lead screw, stepper motor, servo motor or gears. For microfabricated devices, suitable interconnects are included.

Referring again to FIG. 4, once the fritted capillaries 45 are sandwiched in the frame jig 55 and the compression connection 46 has been made, the capillaries 45 are packed using a typical protocol For example, a slurry of 200 µg of 3 µm silica packing material in 1 mL of 60:40 methanol/propanol is ultrasonicated prior to being loaded into a stainless steel packing reservoir 42 or other suitable vessel. A magnetic stir bar is placed in the reservoir to keep the particles in suspension during the packing process by magnetic stirring. The valve 48 is positioned such that the fluid delivery system 41 is in-line with the packing reservoir 42 and a fritted capillary 45. A packing solvent mixture, such as 90% methanol in water, is pumped at high pressure (gradual ramp to and then holding at the desired psi value) to load the packing material into the fritted capillary. It is understood that alternative fluid compositions are suitable. In one embodiment the packing pressure is from 1 to 100,000 psi.

When the packed bed reaches a user-defined, pre-determined length, a photoelectric bed packing sensor 43 terminates the packing process by sending a signal to a controller, which in turn causes the valve 48 to switch. A second reservoir 47 containing a slurry is placed in-line between the fluid delivery system 41 and the packed capillary. In one embodiment the slurry contains 200 µg of spherical, non-porous, non-carbon containing, 5 µm silica particles in 1 mL of 60:40 methanol/propanol. The valve 48 remains in this position for a short period of time allowing for a sufficient amount of 5 µm particles to pack at the head of the column for a second frit to eventually be made via sintering or another bonding method. The valve 48 then turns to a third position where the fluid delivery system 41 is directly in-line with the compression connection 46, bypassing the two reservoirs 42 and 47. The fluid delivery system continues to deliver the packing solvent through the column bed, compacting and settling the stationary phase. The flow from the fluid delivery system is gradually reduced, allowing a slow depressurization of the nascent column in order to avoid disturbances of the packed bed by a sudden change in backpressure. It is understood that, different size particles can be utilized depending on the application. It is further understood that the column bed precursor material may be particles or beads, and that they may be pretreated and/or pre-polymerized. Both slurry and dry materials are suitable. In another embodiment the packing system further provides energy, sonication, vibration, heat, cooling, light, microwave, positive pressure, negative pressure, low frequency energy or high frequency energy.

Common switching valves are susceptible to causing sudden changes in backpressure. The optional pressure release valve 49 shown in FIG. 4, is equipped with an actuator to minimize any potential disturbances in the packed column bed. As packing solvent is continuously delivered to the column, the disturbances created by the valve switching positions are minimal. In one embodiment a backpressure release valve 49, as shown in FIG. 4, is optionally employed to release the backpressure in a well controlled manner using a slow pressure release restrictor vent 40. In yet another embodiment switching valves for directing various fluids are used.

Figure 7A:
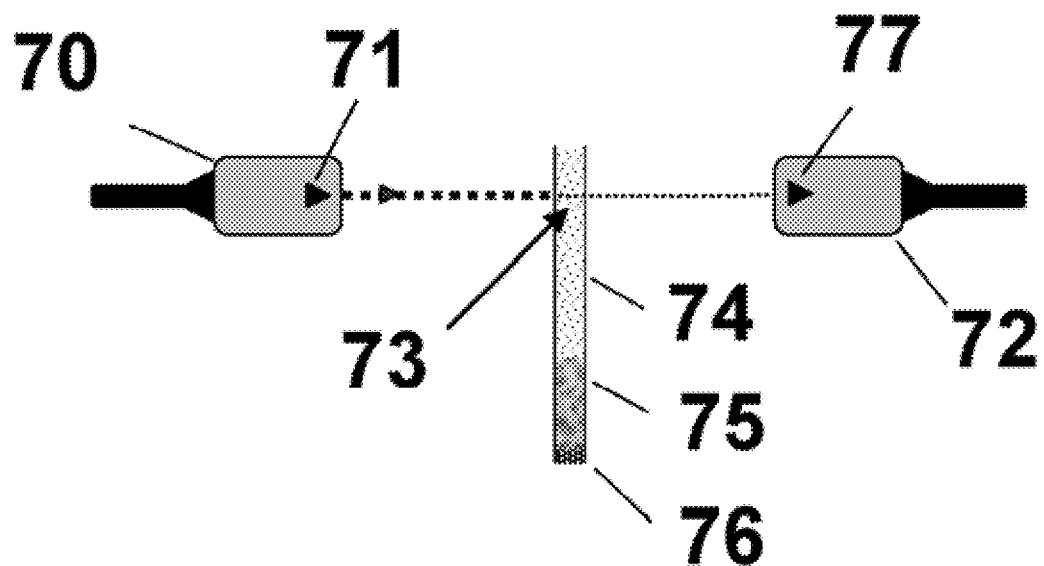
FIG. 7A shows a schematic of a photoelectric sensor using transmission. Once the column bed length reaches the "column bed stop", which is determined by the position of the photoelectric sensor, the sensor will automatically stop the packing process. Figure is not drawn to scale.
Figure 7B:
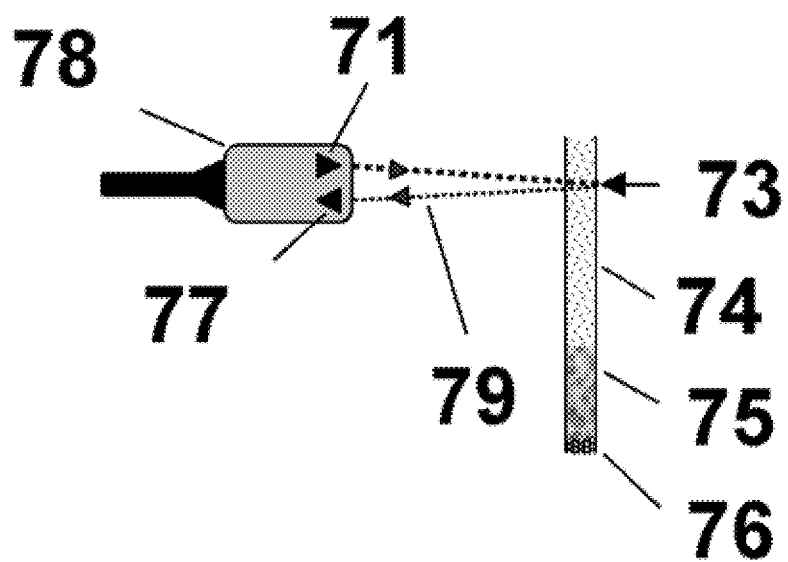
FIG. 7B shows a schematic of a photoelectric sensor using reflection. Once the column bed length reaches the "column bed stop", which is determined by the position of the photoelectric sensor, the sensor will automatically stop the packing process. Figure is not drawn to scale.

As shown in FIG. 7A, a sensor is used to terminate the packing process when the column bed grows to the desired length. This sensor consists of a transmitter 70 and receiver unit 72. The transmitter 70 emits a laser beam from a light-emitting element 71. In one embodiment the light-emitting element is a laser diode. The beam is focused such that it traverses the fritted capillary 74 at the desired point of column bed 73 termination. For example, the laser focuses across the capillary 74 15 cm from the frit 76 when a 15 cm long column is desired. The frame jig and translational stage accurately position the capillary 74 in-line with the beam. As the bed 75 grows and enters the beam region, the amount of light detected by the light-receiving element 77 decreases. The decrease in detected light translates into a lower voltage output by the receiver 72. Once a threshold value is reached, the system terminates the column packing process. As shown in FIG. 7B, in an alternative embodiment, the photoelectric sensor 78 contains both a light-emitting 71 and light receiving element 77 and measures reflected light 79 as opposed to transmitted light. In yet a further embodiment both transmitted and reflected photoelectric sensor types are used in combination. It is understood that the sensor is not limited to a light-based mechanism. In an alternative embodiment optical image, density, sonication, vibration, energy wave, or other detection methods are used to detect any voids. The sensors are also useful for monitoring and controlling chemical processes or reactions.

In one embodiment a single channel has one or more sensors. Alternatively, an array of channels contains one or more sensors. Furthermore the sensor(s) are capable of controlling one or more fluid delivery options. The sensor feedback can control the input for one or more streams for a given channel. The sensor location is either fixed or adjustable. In the embodiment where the sensor is adjustable, the sensor position optionally dynamically changes over the course of the process being monitored.

In one embodiment the device may use a single compression fitting mechanism so that each fritted capillary is slurry-packed one at a time. In an alternative embodiment a plurality of mechanisms are implemented for parallel packing. When the packing process for one particular column is complete, the compression mechanism disengages and the frame jig is indexed so that the next fritted capillary comes in-line. The compression mechanism re-engages with the new fritted capillary and the packing process begins for the newly engaged capillary. In this manner, all the fritted capillaries held within the frame jig are packed sequentially in an automated fashion. The time needed to pack a column is determined by column length, packing pressure, and particle size. In one embodiment the typical pack time is approximately 10 minutes. It is understood that the pack time may range from 0.1-1440 minutes for varying applications. The frame jigs are capable of holding one or more capillaries or channel holding devices such as microchip-based devices. In another embodiment an automated frame jig loader is utilized to allow for high volume column manufacturing. In yet another embodiment, multiple compression connection mechanisms, operating independently, are used to pack capillaries present in a single frame jig.

This system/method allows for the manufacturing of small bore LC columns with an automated continuous process. The automated process lends to a higher yield of consistent, reproducible product. Consequently, more reproducible small bore LC columns are produced.

In an alternative embodiment the automated multi-column packing system is utilized for microchip-based and microfabricated devices. The channels are addressed by the automated sealing mechanism and delivery system. The channels or features are monitored by the sensor system in a similar fashion as for controlling the packing process.

Automated Optical Packed Bed Assessment Device

Figure 8:
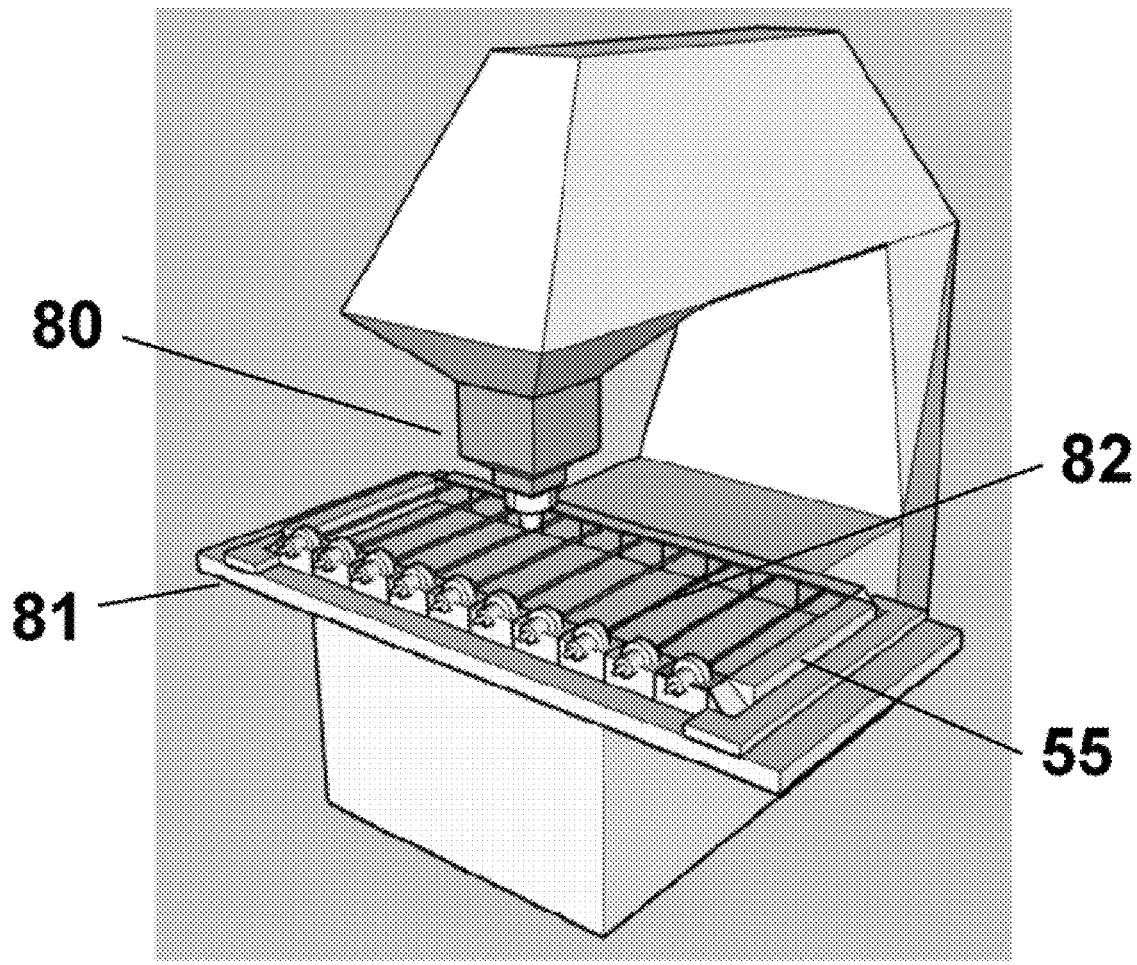
FIG. 8 shows the automated optical packed bed assessment system. This system accepts the same frame jig used in the column packing system. The output from the optical viewing system is provided to the pattern recognition software, which then determines if any column defects are present. The figure is not drawn to scale as the columns and ferrules have been enlarged to be viewed more easily.

Referring to FIG. 8, the optical packed bed assessment device is shown. The frame jig 55, between which the columns 82 are sandwiched, is removed from the automated multi-column packing system as one amalgamated unit. This frame jig 55 is then inserted, with by hand or via an automated fashion, directly into the automated, optical packed bed assessment device. Alternatively the optical packed bed assessment device is part of the packing device. This device consists of a light source (not shown), an optical charged-coupled device (CCD) detection system 80, a translational stage 81 which accepts and secures the frame jig containing the small bore LC columns 82, and pattern recognition software (not shown).

Figure 2A:
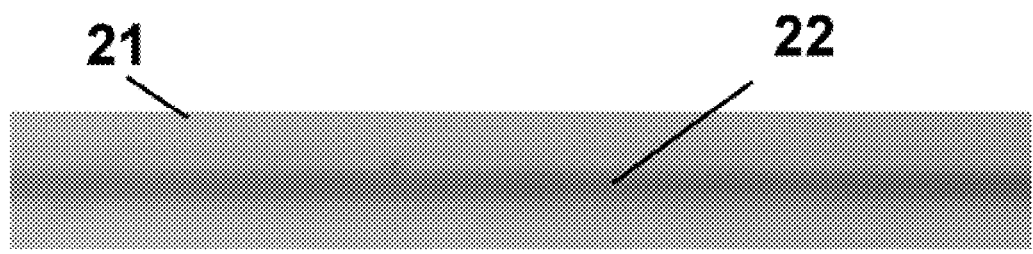
FIG. 2A is a magnified image (500×) of a column using reflected light.
Figure 2B:
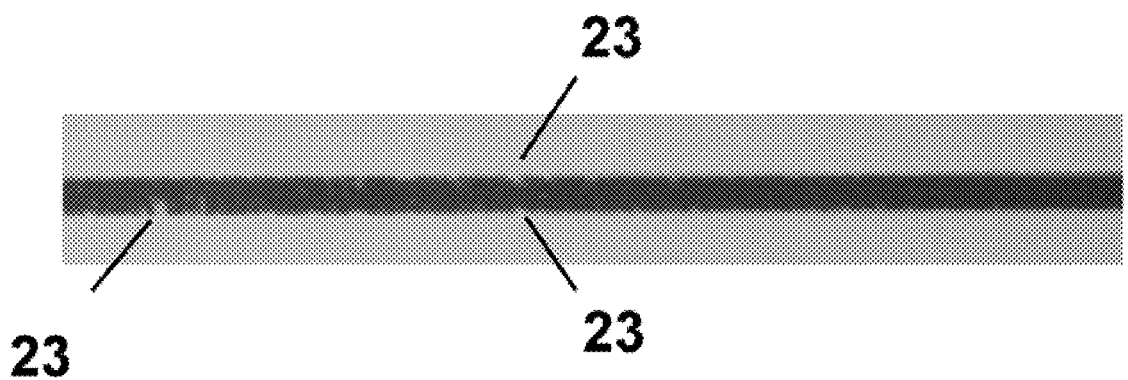
FIG. 2B is a magnified image (500×) of the same view as FIG. 2A, but using transmitted light. Transmitted light provides better contrast than reflected light for viewing packed bed defects which are visible only in FIG. 2B and are indicated.

This system examines the packed small bore LC columns and identifies any packing inconsistencies, such as voids. To accomplish this, a light source, located beneath the small bore LC columns, transmits light through the columns which is then detected by an optical CCD system, located above the small bore LC columns. As shown in FIGS. 2A and 2B, the voids 23 in the packed bed 22 within the capillary 21 are clearly visible by detecting the transmitted light. In an alternative embodiment reflected light, as shown in FIG. 2A, or a combination of transmitted and reflected light is used. In one embodiment the optical system, which is composed of the light source, optics, and CCD detector, is fixed in space, while the frame jig is mounted on a translational stage. The stage moves such that the entire length of the small bore LC column is examined before the system indexes to the next column contained in the frame jig, and then proceeds to examine the entire length of this second column, and then examines all other columns in the frame jig. Alternatively the stage may be stationary with a mobile optics system.

As relatively high magnification is required to detect imperfections, the columns are scanned by the optical system at approximately 1 mm$^2$ field of view segments. Alternatively, various magnifications are used depending on the required magnification for viewing the critical dimensions. Post-image processing occurs via pattern recognition software. The system is able to discern areas devoid of packing material, areas with loose packing, and areas with overly dense packing within the column bed. Consequently any packing inconsistencies are unambiguously identified. In one embodiment the scan rate of the system is approximately 8 cm per minute, so that a 15 cm column can be fully examined in less than 2 minutes. This examination time may be decreased by using a faster scanning or higher resolution camera reducing the analysis to only a few seconds per column or device.

The frame jig and translation stage receiver may be machined to a high tolerance to hold the capillaries in place or pattern recognition software may be used to compensate to keep the desired region in the field of view during scanning or assessment. Additionally, each frame jig has fiducial marks to aid in calibrating the position of the stage relative to the optics during setup. A common approach is that three extents are measured and then the theta angle is determined. The coordinate information obtained then allows for any non-squareness in the frame jig or stage to be corrected through adjustment of encoder motor movement. This correction ensures that the frame and stage move linearly over a large range of travel. This correction is imperative as larger frames and travels are used for higher capacity systems. Optionally, an autofocus system is utilized to keep the bed in the focal plane.

In addition to aiding system alignment, the pattern recognition software also evaluates the output from the optical system. Furthermore, in another embodiment the pattern recognition software is capable of identifying any defects in the packed column bed. Optionally, an additive or marker, such as a dye or contrasting material, is added to aid in defect identification. Once the entire length of each column is scanned by capturing sequential fields of view from the optical system, data processing will be performed. The scan field images are searched against a column defect database. In one embodiment the analysis is conducted in real-time on a live image or on a previously acquired image. The pattern recognition software is programmed to consistently and unambiguously identify any packing anomalies based on the database. The software has pass/fail criteria based on the defect and defined thresholds, and for any column locations that fail the criteria, the operator will be able to review the stored image, as well as the intensity, contrast, and contour plots. This approach allows an operator to review and confirm the suspect region of the column, if desired. Furthermore, the pattern recognition software can be programmed to output a summary report of the inspection results for operator review.

Figure 3A:
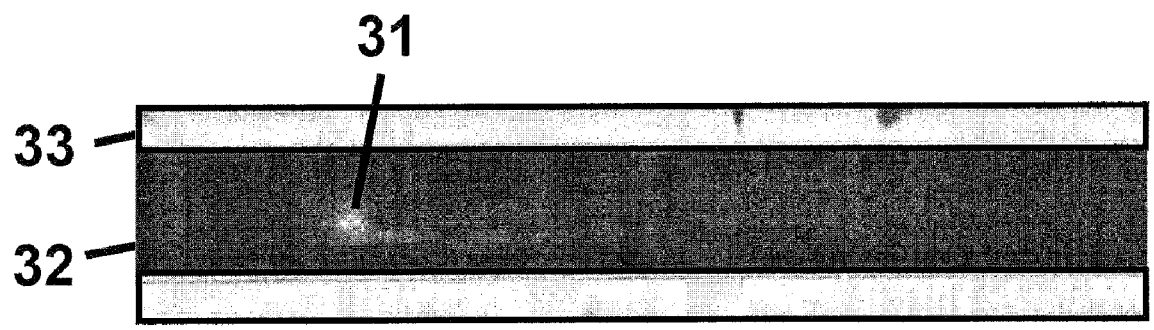
FIG. 3A is a magnified image (1000×) of a commercial 75 μm id small bore LC column. Transmitted light was used to observe void regions in the packed bed as indicated. Pattern recognition software was used to identify the void region and calculate the associated area.
Figure 3B:
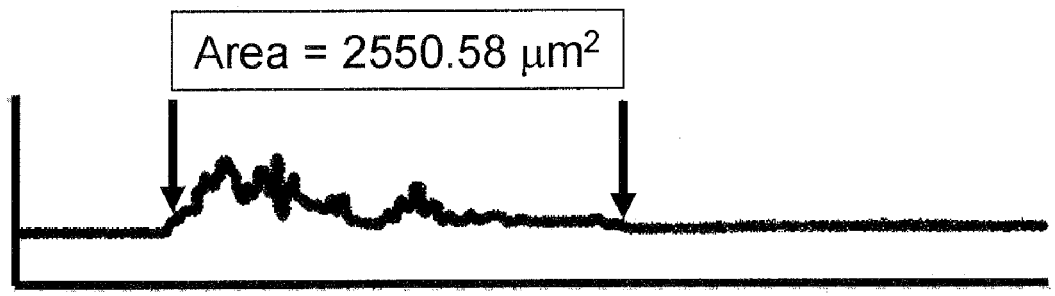
FIG. 3B is a plot of transmitted light vs column bed length for the commercial 75 μm id small bore LC column shown in FIG. 3A. It is apparent that the void region gives rise to an increase in transmitted light detected by the optical system.
Figure 3C:
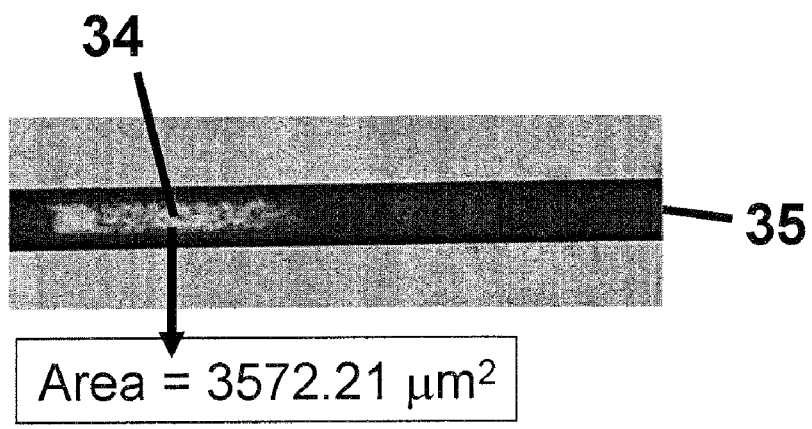
FIG. 3C is a magnified image (1000×) of a commercial 25 μm id small bore LC column. Transmitted light was used to observe void regions in the packed bed as indicated. Pattern recognition software was used to identify the void region and calculate the associated area.

As shown in FIG. 3A-3C void regions 31 within commercially available columns can be detected by pattern recognition software. FIG. 3A shows a 1000× magnified image of a capillary 33 having a packed bed 32. The void region 31 is clearly visible. Furthermore, pattern recognition software is capable of identifying this void region 31 and calculating the area as shown. Referring to FIG. 3B, there is shown a plot of transmitted light vs column bed length for the column shown in FIG. 3A. It is apparent that the void region gives rise to an increase in transmitted light detected by the optical. Additionally, the associated scan data, as shown in FIG. 3B, can be exported into Excel files so macros scripts may be written for statistical analysis. This allows for long-term process monitoring and comparison of intra and inter-batch variability. Real-time Statistical Process Control (SPC) analysis is also possible. Consequently, the automated optical packed bed assessment system is capable of thoroughly investigating and assessing the entire column bed of every column manufactured. As each scan field is capable of being captured, the images can be digitally "stitched" together providing a high magnification view of the entire column. This compiled image may then be provided to the customer with each column greatly improving the inspection confidence.

Referring to FIG. 3C, there is shown a 1000× magnified image of a commercial available 25 μm id small bore LC column. Transmitted light was used to observe void regions 34 in the packed bed 35 as indicated and pattern recognition software was used to identify the void region 34 and calculate the associated area shown.

It is commonly accepted that small bore LC column performance is defined by the uniformity of the packed bed. Since the packed bed assessment system is evaluating the fundamental cause of poor column performance, no analytical runs for quality control testing of the column are necessary.

In addition to the assessment of particle-based stationary phases, this optical inspection approach is further useful for assessing other forms of stationary phases such as polymeric, sol-gel, or chemically bonded.

The packing and optical inspection may be achieved with either one integrated device or two separate devices. As the column packing step is much slower than the quality control testing, for high volume manufacturing, having several column packing instruments to every one quality control testing instrument can be envisioned. Another advantage of splitting these two functions into their own instrument is in the event of a malfunction, only one manufacturing step would be shut down instead of two.

Once the assessment of the column beds is complete, the columns are removed from the frame jig and a second porous, sol-gel frit is made at the column entry. In one embodiment, the spherical, non-porous, non-carbon containing, particles that were loaded into the column at the end of the packing process are formed into a frit by applying a "Kasil" solution of potassium oxide, silicon dioxide, and formamide. At the inlet end of each column approximately 1 μL of the "Kasil" solution is drawn-up into the column through capillary action and is mixed with the particles. The solution can be dried at room temperature (approximately 10 min), allowing polymerization and porous frit formation. This frit formation step occurs after the column assessment so that the columns can remain in the frame jig from column fabrication through bed assessment. This inlet frit provides extra stability to the packed-bed, and this is especially important during shipment of the column to the customer. If this inlet frit were not present, the bed could un-pack during shipment, and although the column would "re-pack" when mobile phase is pumped through, there is great potential for packed-bed inconsistencies to be introduced during the "re-packing" process. In one embodiment the final column is packaged in a protective, rigid, tamper-proof package for extra stability. It is understood that the inlet frit could be made by methods other than sol-gel or could be absent altogether.

Figure 9A:
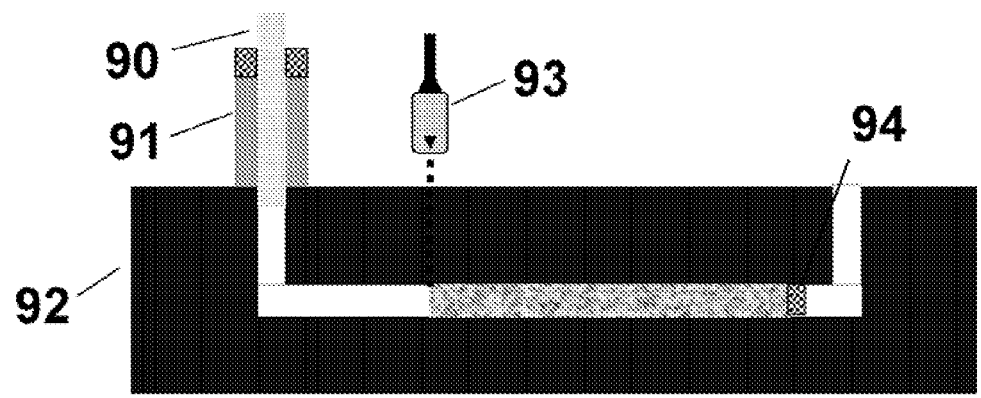
FIG. 9A shows a channel in a microchip capable of being packed using the column packing system described above. The fill head compresses against the chip, forms a seal and delivers the packing material into the channel. The packing sensor detects when the channel has been packed to the desired length.
Figure 9B:
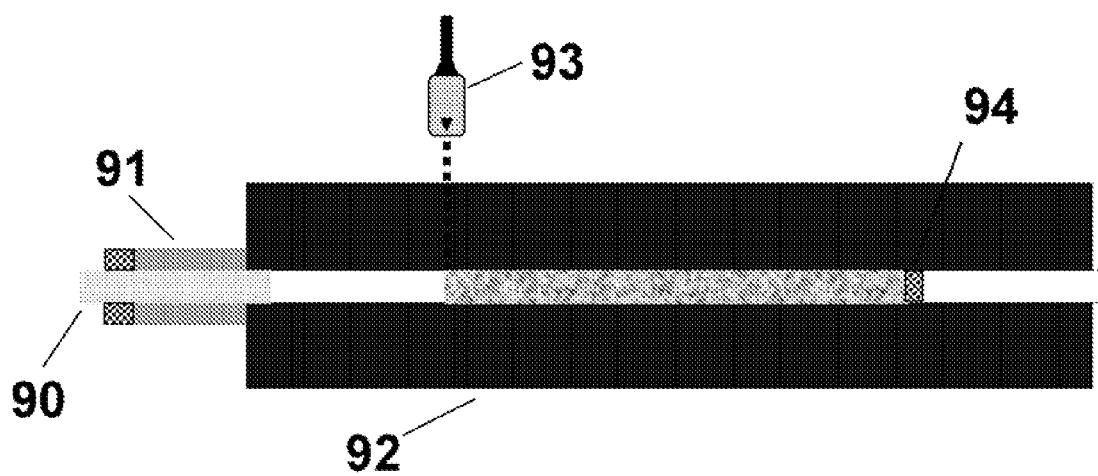
FIG. 9B shows a channel in a microchip that is capable of being packed from the edge of the chip using the column packing system described. The fill head compresses against the edge of the chip, forms a seal and delivers the packing material into the channel. The packing sensor detects when the channel has been packed to the desired length.

FIGS. 9A and 9B shows a channel in a microchip 92 capable of being packed using the column packing system described above. The fill head 91 contains a delivery tube 90 and the fill head 91 compresses against the chip 92 to form a seal for delivering packing material into the channel. The frit 94 prevents flow of packing material past the point in the channel that the frit 94 is located. The packing sensor 93 detects when the channel has been packed to the desired length.

EXAMPLE

A slurry of stationary phase sorbent is delivered by a fluid delivery system to a capillary. This capillary has a frit formed at one end which prevents the stationary phase from exiting the column. The frit can be formed by a variety of different methods which include, but is not limited to, porous filters, scintering methods, restrictors and tapers including nanoelectrospray emitters, porous ceramic plugs, sol-gel technology, unions containing stainless steel screens, and self-assembled particles. A compression fitting mechanism forms a leak-tight connection between the slurry reservoir and the fritted capillary. As the slurry is pumped into the capillary, the frit allows for the formation of a packed bed within the capillary. The system has a sensor which will terminate the slurry delivery to the capillary when the packed bed reaches the desired, predetermined length. When the packed bed formation is complete, the compression fitting mechanism disengages with the nascent column, translational stages index to the next fritted capillary, and the compression fitting mechanism engages with this second fritted capillary. A frame jig securing multiple, fritted capillaries is located on a translational stage, allowing for multiple columns to be manufactured in an automated fashion.

Following the packing process, the frame jig containing the nascent columns is removed from the packing system and placed into a column assessment system. This system optically assesses the entire packed bed of every column in the frame jig. To accomplish this a light source, located beneath the small bore LC columns, transmits light through the columns which is then detected by an optical CCD system, located above the small bore LC columns. The optical system, which is composed of the light source, optics, and CCD detector, is fixed in space, while the frame jig is mounted on a translational stage. The stage moves such that the entire length of the small bore LC column is examined before the system indexes to the next column contained in the frame jig, and then proceeds to examine the entire length of this second column. As relatively high magnification is required, the columns are scanned by the optical system at approximately 1 $mm^2$ field of view segments. The field of view depends on the optical system and feature sizes as well as the camera resolution and frame rate. One or more scan types may be performed such as bright field, dark field, reflection, transmission, DIC, normaski, phase contrast, IR, etc. The optical system can use visible, UV, IR, thermal or vibrational energy. Live or post-image processing occur via pattern recognition software. All columns contained within the frame jig are examined in this manner. The system is able to discern areas devoid of packing material, areas with loose packing, and areas with overly dense packing within the column bed. Consequently any packing inconsistencies will be unambiguously identified.

Once the assessment of the column beds is complete, the columns are removed from the frame jig and a second frit may be formed at the column entry. If formed, this inlet frit provides extra stability to the packed-bed, and would be especially important during shipment of the column to the customer.

The system is useful for packing devices other than columns such as reactors, vessels, and substrates. Alternatively, a fluid may be delivered that could polymerize in the device. Delivery may be achieved with positive or negative pressure, and/or capillary action.

The automated connection/compression fluid delivery system allows for the connections of one or more liquid or gas streams in tubing or capillaries. The connections may have integrated functionality within the fitting such as particle filters, frits, guard columns, trap columns, reactors, injectors, or particle, monolithic, or affinity stationary phases, or those alike. The fittings may be casted, molded, machined, monolithic in nature, or compiled from multiple components. The compression mechanism and fittings may hold up to 100,000 psi, however this may increase as technology advances. The fitting receives a constant pressure in the axial direction. The constant compression connection of the instant invention is less prone to leaks as compared to the conventional thread-type chromatography connections as conventional fittings often fatigue, slip, or loosen over time and require additional force to be reapplied by further tightening of the fittings. The fittings may be used to connect preparative, analytical, micro, nano, and pico chromatography columns, as well as CE, CEC, micelles capillary tubes, flow-through reactors, cartridges, sample injectors, and chip-based separation structures and features, such as channels that are packed or unpacked. The system can be used for reversed-phase, normal phase, flash, supercritical fluid, or affinity applications. In one embodiment the system can be used at 1 mL/min to 10 mL/min flow rates.

The automated delivery approach here may also be used to deliver fluid for other process functions and chemical pre-treatment, post-treatment, priming, washing, derivatizations, polymerization, modifications, grafting, pre-conditioning, and post conditioning. Examples include chemical substrate loading, chemical support phases, oxidation, reduction, acids/bases, chelating agents, depletion, derivatization, chemical modifications, precursors, and polymerization. The delivery approach is also useful for pre-filling post-treatment or purging devices.

The optical assessment system may look at a part in a jig or the part may be transferred to another type of preferred jig or holding/mounting mechanism.

Although the preferred embodiment of the present invention is shown, it will be understood to those skilled in the art that other embodiments can be used without departing from the scope of the invention. For example, in the fitting assemblies shown in the figures, the ferrules and receiving ports can be interchanged.

The invention has been described with reference to a preferred embodiment. However, it will be appreciated that variations and modifications can be effected by a person of ordinary skill in the art without departing from the scope of the invention.

The invention claimed is:

1. An automated column packing system comprising:
   a frame jig capable of holding a plurality of columns, each column comprising a channel having an open end and a porous fritted end;
   a compression fitting mechanism capable of making a fluid-tight seal with the open end of the column channel;
   a fluid delivery system in fluid communication with the compression fitting mechanism the fluid delivery system comprising;
      a fluid source
      at least one reservoir containing packing material,
      a fluid control valve, and
      a controller in signal communication with the fluid control valve;
   a sensor in signal communication with the controller and capable of monitoring the packed-bed length of the column during filling; and
   a translational stage secured to the frame jig and capable of moving the frame jig relative to the compression fitting mechanism.

2. The automated column packing system of claim 1 wherein the packing material comprises:
   stationary phase particles or sorbent material.

3. The automated column packing system of claim 1 wherein the compression fitting mechanism is capable of sealing up to 100,000 PSI.

4. The automated column packing system of claim 1 further comprising a packed-bed assessment system.

5. The automated column packing system of claim 4 wherein the packed-bed assessment system comprises:
   optics capable of viewing the column;
   an energy or light source directed at the column;
   a detector capable of measuring characteristic changes in energy or light reflected from or transmitted through the column;
   and
   a storage system capable of storing image data, wherein the characteristic changes in energy or light represent voids or density changes in the packing material of a packed-bed column.

6. The automated column packing system of claim 5 wherein the packed-bed assessment system further comprises a pattern recognition system capable of comparing images to a defect database.

7. The automated column packing system of claim 5 wherein the packed-bed assessment system further comprises:
   a display for viewing a magnified image of the changes in energy or light reflected from or transmitted through the column.

8. The automated column packing system of claim 1 wherein the column comprises a small bore tube or a microchip.

9. The automated column packing system of claim 1 wherein the channel comprises an inner diameter of from 1 to 1000 microns.

10. The automated column packing system of claim 1 wherein the fluid delivery system delivers a slurry of packing material to the column channel.

11. The automated column packing system of claim 1 wherein the column is a capillary column, microfabricated channel, nanofabricated channel, reactor, vessel, cartridge, machined assembly, or molded assembly.

* * * * *